United States Patent [19]
Haber et al.

[11] Patent Number: 6,140,265
[45] Date of Patent: *Oct. 31, 2000

[54] CATALYST FOR CROSS-COUPLING REACTIONS

[75] Inventors: Steffen Haber, Germersheim; Norbert Egger, Wiesbaden, both of Germany

[73] Assignee: Clariant GmbH, Frankfurt, Germany

[ * ] Notice: This patent is subject to a terminal disclaimer.

[21] Appl. No.: 09/000,128

[22] PCT Filed: Jul. 24, 1996

[86] PCT No.: PCT/EP96/03266

§ 371 Date: May 22, 1998

§ 102(e) Date: May 22, 1998

[87] PCT Pub. No.: WO97/05151

PCT Pub. Date: Feb. 13, 1997

[30] Foreign Application Priority Data

| Jul. 25, 1995 | [DE] | Germany | 195 27 118 |
| Sep. 25, 1995 | [DE] | Germany | 195 35 528 |
| May 17, 1996 | [DE] | Germany | 196 20 023 |

[51] Int. Cl.$^7$ .............. B01J 31/00; B01J 27/14; B01J 27/186; B01J 27/187; C07C 255/00

[52] U.S. Cl. .......... 502/162; 502/150; 502/152; 502/155; 502/156; 502/168; 502/208; 502/213; 502/216; 502/223; 558/357

[58] Field of Search .................... 502/150, 155, 502/156, 162, 172, 152, 208, 213, 216, 223, 168; 558/357

[56] References Cited

U.S. PATENT DOCUMENTS

| 4,229,606 | 10/1980 | Nozaki | 585/509 |
| 4,474,978 | 10/1984 | Drent et al. | 560/24 |
| 4,849,542 | 7/1989 | Drent | 560/175 |
| 5,347,045 | 9/1994 | Herrmann et al. | 562/35 |
| 5,481,045 | 1/1996 | Herrmann et al. | 568/454 |
| 5,525,566 | 6/1996 | Keim et al. | 502/162 |
| 5,565,398 | 10/1996 | Herrmann et al. | 502/166 |
| 5,686,608 | 11/1997 | Haber | 544/316 |
| 5,712,403 | 1/1998 | Sato et al. | 556/19 |
| 5,736,480 | 4/1998 | Davis et al. | 502/155 |
| 5,756,804 | 5/1998 | Haber et al. | 558/411 |
| 5,919,930 | 7/1999 | Haber et al. | 544/238 |

FOREIGN PATENT DOCUMENTS

| 571819 | 5/1993 | European Pat. Off. . |
| 679619 | 11/1995 | European Pat. Off. . |

OTHER PUBLICATIONS

International Search Report.

Derwent Abstract—DE 19527118, May 16, 1997.

Derwent Abstract—DE 19535528, Nov. 20, 1997.

Derwent Abstract—DE 19620023, Nov. 25, 1997.

*Primary Examiner*—Mark L. Bell
*Assistant Examiner*—Patricia L. Hailey
*Attorney, Agent, or Firm*—Miles B. Dearth; Scott E. Hanf

[57] ABSTRACT

A catalyst system, in particular for carrying out cross-coupling reactions is obtainable by reacting
 a) a palladium(II) compound with
 b) a water-soluble phosphine ligand and
 c) a sulfoxide or polyhydric alcohol.

10 Claims, No Drawings

CATALYST FOR CROSS-COUPLING REACTIONS

The invention relates to a palladium catalyst comprising a water-soluble phosphine ligand, preferably for carrying out cross-coupling reactions, a process for its preparation and also its use in cross-coupling reactions.

Cross-coupling reactions of aromatic boron compounds, e.g. boronic acids, and aromatic halogen compounds or perfluoroalkylsulfonates have for some years been used to an increasing extent for building up polycyclic aromatic systems. For example, such processes are used for producing active compounds for pharmaceuticals and components of liquid crystal mixtures.

However, the catalysts customarily used, e.g. $Pd[P(Ph_3)]_4$ or $PdCl_2(4PPh_3)4NaBH_4$, give the coupling products in appreciable yields only when bromoaromatics or iodoaromatics are employed. The high costs of these starting compounds make economical scale-up of the processes to a production scale difficult.

EP-A 0 372 313 discloses palladium catalysts comprising water-soluble phosphine ligands which are used, for example, in the cross-coupling reaction of alkynes with allenes.

The systems described always contain palladium in the oxidation state (0).

EP-A 0 694 530 describes a process for preparing polycyclic aromatic compounds by cross-coupling aromatic boron compounds with aromatic halogen compounds or aromatic perfluoroalkylsulfonates using palladium catalysis in the presence of at least one water-soluble complexing ligand, wherein the reaction medium comprises an aqueous phase and an organic phase and the palladium is added in the form of a palladium compound soluble in the organic phase.

Although very good results are achieved using this process, there is still room for improvements, particularly with regard to the use of inexpensive chloroaromatics as starting material.

It has now surprisingly been found that palladium catalysts having a particularly high activity can be prepared by reaction of palladium(II) compounds, water-soluble phosphine ligands and a sulfoxide or a polyhydric alcohol.

The present invention accordingly provides a catalyst system, in particular for carrying out cross-coupling reactions, obtainable by-reacting a) a palladium(II) compound with
b) a water-soluble phosphine ligand and
c) a sulfoxide or polyhydric alcohol.

The invention further provides a process for preparing a catalyst system, in particular for carrying out cross-coupling reactions, which comprises reacting a) a palladium(II) compound with
b) a water-soluble phosphine ligand and
c) a sulfoxide or polyhydric alcohol.

The invention likewise provides for the use of a catalyst system obtainable by reacting a) a palladium(II) compound with
b) a water-soluble phosphine ligand and
c) a sulfoxide or polyhydric alcohol for carrying out cross-coupling reactions.

Catalyst systems according to the invention have a particularly high activity and it is possible to use them a plurality of times. They are also suitable, in particular, for coupling reactions in which chloroaromatics can be used as starting materials.

Suitable components a are palladium(II) compounds, preferably palladium(II) salts, tetrachloropalladic acid or its salts, preferably alkali metal salts. Preferred compounds are, for example, palladium acetylacetonates, palladium halides, allylpalladium halides and palladium biscarboxylates, particularly preferably palladium acetylacetonates, palladium (II) halides, tetrachloropalladic acid and its salts.

Compounds which are very particularly suitable as component a are $Pd(II)Cl_2/3$ NaOAc, $Pd(ac)_2$, $K_2PdCl_4$, $Na_2PdCl_4$, $K_2Pd_2Cl_6$, $Na_2Pd_2Cl_6$ and $H_2PdCl_4$.

It is naturally also possible to use mixtures of two or more palladium compounds as component a.

In a preferred embodiment of the invention, the catalyst system comprises one or more additives such as sodium acetate which act as solubilizer for the palladium compound in the system sulfoxide or polyhydric alcohol and, if desired, water. Particular preference is given to using sodium acetate, in particular in a molar ratio of from 1 to 4, preferably 3, based on the palladium compound.

Suitable water-soluble phosphine ligands are tri-n-alkylphosphines, triarylphosphines, dialkylarylphosphines, alkyldiarylphosphines and heteroarylphosphines preferably provided with carboxylate or carboxylic acid, ammonium, phosphonium, sulfonate or sulfonic acid, phosphonate or phosphonic acid groups or with polyalcohols having a suitable number of hydroxy functions or polyalkylene glycols having a suitable chain length, where the three substituents on the phosphorus can be identical or different and chiral or achiral and one or more of the substituents can link the phosphorus groups of a plurality of phosphines and part of this linkage can also be one or more metal atoms.

Particular preference is given to using water-soluble phosphines which have at least one aryl group on the phosphorus, i.e. triarylphosphines, diarylalkylphosphines and dialkylarylphosphines.

Particular preference is given to using water-soluble phosphines of the formulae (I) to (VII),

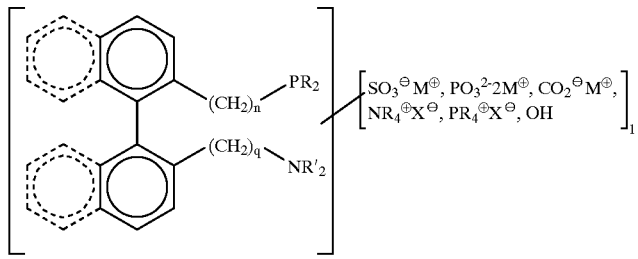

(I)

(II)
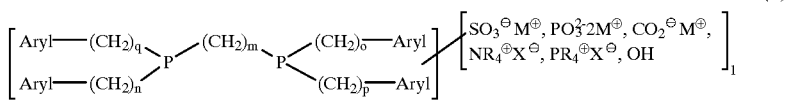

(III)
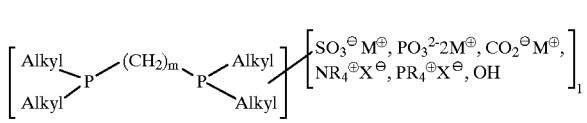

(IV)
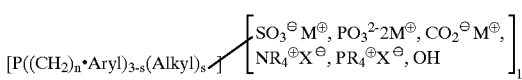

(V)

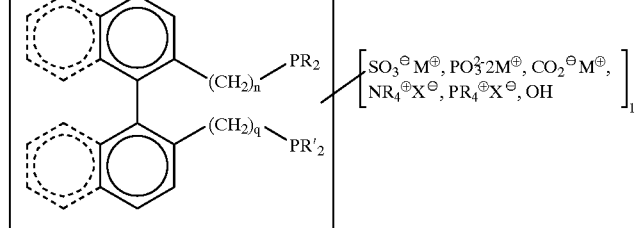

(VI)
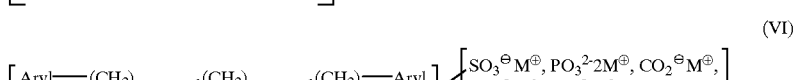

(VII)
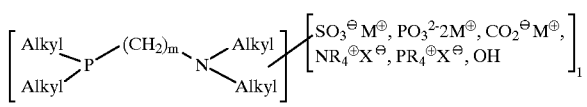

where the symbols and indices have the following meanings:

Aryl: a phenyl or naphthyl group which may also bear one or more substituents R;

Alkyl: a straight-chain or branched alkyl group having from 1 to 8 carbon atoms;

R,R': alkyl, aryl or aralkyl having from 1 to 18 carbon atoms;

M: alkali metal, alkaline earth metal or $NR_4$;

X: halogen, $BF_4$, $OSO_2CF_3$, $1/2[SO_4]$;

l,m: 1 to 8;

n,o,p,q: 0, 1 to 8;

s: 0, 1 to 3.

Examples of particularly preferred water-soluble complexing ligands are shown below:
(R is, unless indicated otherwise, as defined for the formulae (I) to (VII))

1. Sulfonated Phosphines

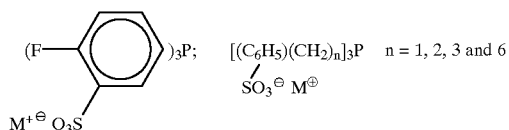

-continued

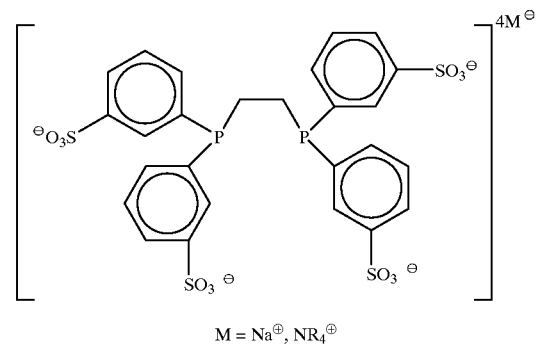

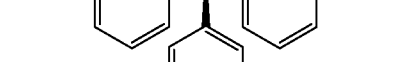

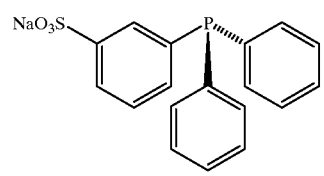

-continued

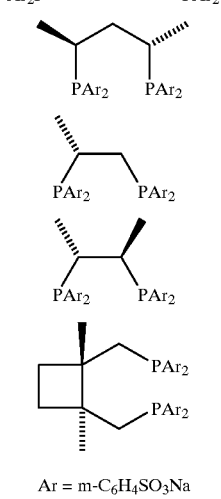

Ar = m-C₆H₄SO₃Na

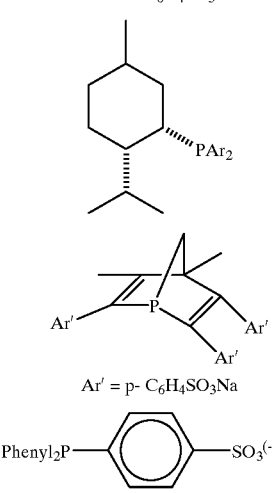

Ar' = p- C₆H₄SO₃Na

Phenyl₂P—⟨⟩—SO₃⁽⁻⁾Na⁽⁺⁾

$R_{3-n}P(p-C_6H_4SO_3K)_n$ R=C₆H₅, 2-Pyridyl, 3-Pyridyl; n=1–3
$P[p-OC_6H_4SO_3(NH(i-octyl)_3)]_3$

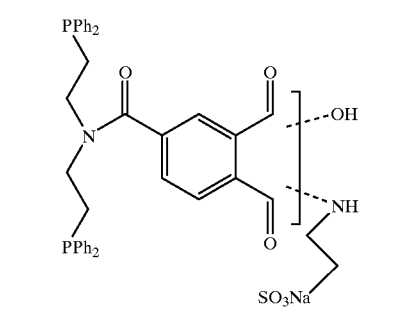

(C₆H₅)₂PCH₂CH₂SO₃⁽⁻⁾Na⁽⁺⁾

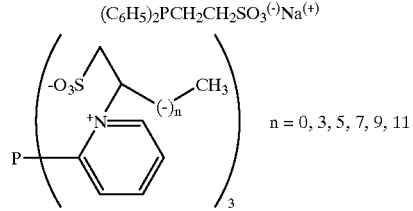

n = 0, 3, 5, 7, 9, 11

2. Phosphines Having Quatemized Aminoalkyl and Aminoaryl Substituents

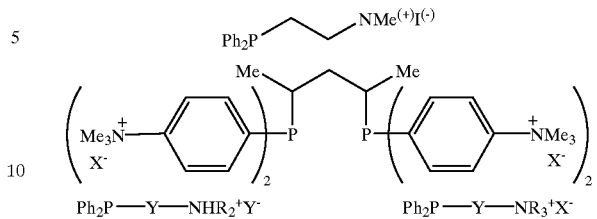

$Y=$—CH₂CH₂—, —CH(CH₃)CH₂—, —CH₂CH(CH₃)CH₂—; R=CH₃; X=I⁻, Bu⁻, Cl⁻, OSO₂CF₃⁻, BF₄⁻

3. Carboxylated Phosphines

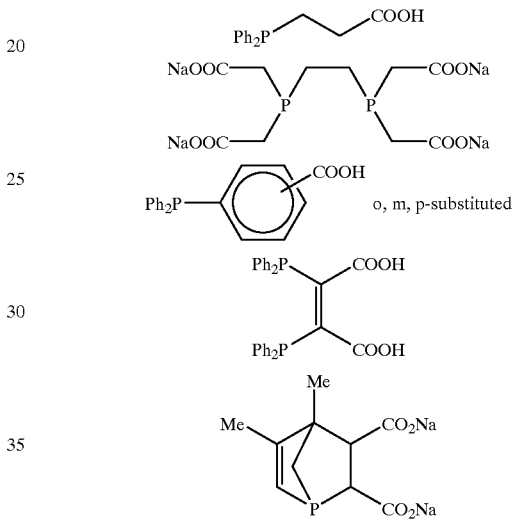

Very particular preference is given to:

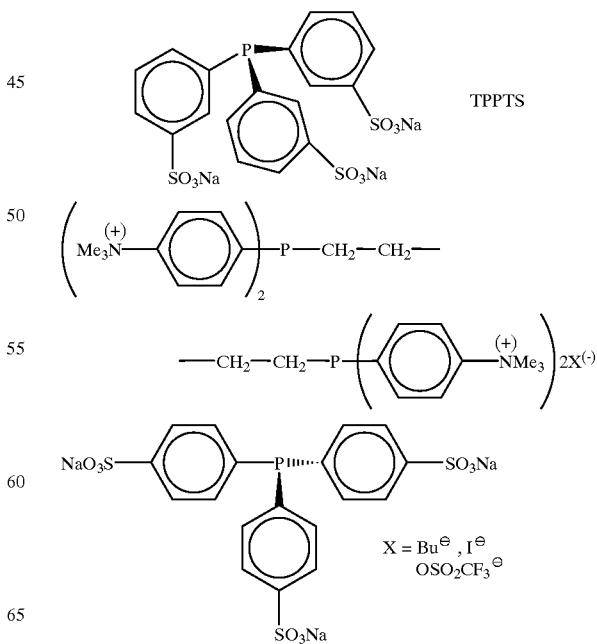

-continued

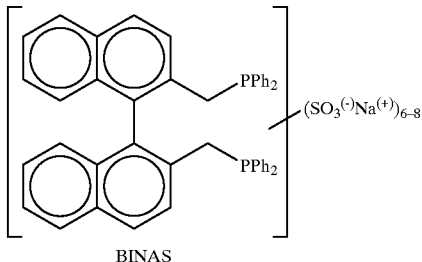

BINAS

It is naturally also possible to use a plurality of phosphorus-containing ligands.

The phosphorus-containing ligands used according to the invention are known per se. Some of them are available as commercial products or they are described together with their synthesis in, for example, Houben-Weyl, Methoden der Organischen Chemie, Georg-Thieme-Verlag, Stuttgart.

Water-soluble ligands can be prepared, for example, by the method of W. A. Herrmann and C. W. Kohipainter, Angew. Chem. Int. Ed. Engl. 1993, 32, 1524 or the literature cited therein. The preparation of BINAS is described in EP-A 0 571 819 or U.S. Pat. No. 5,347,045. An aqueous 0.6 molar solution of the trisodium salt of TPPTS is commercially available (Hoechst AG, Germany).

According to the invention, the phosphorus-containing ligand is used in a ratio of from 1 to 20 phosphorus equivalents, preferably from 2 to 12, particularly preferably from 2 to 6, very particularly preferably 4, based on the Pd compounds.

Preferred polyhydric alcohols are those which are water-soluble. Particular preference is given to glycols, glycerol, oligoglycerides which may also be partially esterified, diethylene, triethylene and tetraethylene glycols or polyethylene glycols or the formula (VIII),

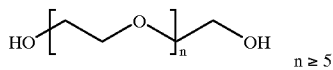

(VIII)

polyhydric alkanols or alkenols such as 1,4-butanediol, 1,3-propanediol, 1,2-propanediol, pentaerythritol, 2-ethylhexane-1,3-diol, 2-(hydroxymethyl)-2-methyl-1,3-propanediol, 2-methyl-2,4-pentanediol, 1,4-cis-butenediol, polyhydric cycloalkanols such as cyclohexanediol, polyhydric alkanols containing aryl groups, e.g. 1-phenyl-1,2-ethanediol, polyhydric aminoalcohols such as diethanolamine, triethanolamine, 2-amino- 2-methyl-1,3-propanediol, 3-(aminomethyl)-1,2-propanediol, 3-amino-1,2-propanediol, 2-amino-1,3-propanediol oxalate, 3-(diethylamino)-1,2-propanediol, ethylenediamine-N,N,N',N'-tetra-2-propanediol, polyhydric iminoalcohols, such as N-butyl-2,2'-iminodiethanol and N-tert.-butyl-2,2'-iminodiethanol, 1,1'-iminodi-3-propanol, N-methyl-2,2'-iminodiethanol, N-phenyl-2,2'-iminodiethanol or compounds such as 1,1',1"-nitrilotri-2-propanol, 1,3,5-tri(2-hydroxyethyl)isocyanuric acid and dihydroxyacetone.

Very particular preference is given to glycol, glycerol, 1,4-butanediol, 1,2-propanediol, triethylene glycol, diethylene glycol, diethanolamine and triethanolamine and among these particularly glycol, glycerol, 1,4-butanediol and 1,2-propanediol.

It is naturally also possible to use a plurality of polyhydric alcohols.

Preferred sulfoxides are those of the formula (IX):

$R^1$, $R^2$ are aliphatic or aromatic hydrocarbons which may, if desired, be substituted or linked to one another.

Particularly preferred sulfoxides are dimethyl sulfoxide (DMSO), diphenyl sulfoxide, methyl phenyl sulfoxide and dibenzyl sulfoxide.

Preference is given to using water-soluble sulfoxides. A particularly preferred water-soluble sulfoxide is DMSO.

It is naturally also possible to use a plurality of sulfoxides or their mixtures, if desired also with polyhydric alcohols.

The polyhydric, water-soluble alcohols or the sulfoxide are preferably added in a weight ratio of from 0.1 to 10,000, based on the palladium(II) compound.

The catalyst system of the present invention preferably comprises water, for example by addition of the phosphine ligands as aqueous solution.

The preparation of the catalyst system of the invention can be carried out according to different variants.

The palladium compound can first be dissolved, for example by dissolving it in the sulfoxide or the polyhydric alcohol with the aid of additives such as sodium acetate, and subsequently be reacted with the phosphine ligand dissolved in water, to form the catalyst system of the invention. However, the catalyst system is also formed when the individual components are mixed at the same time.

To use the catalyst system of the invention, preference is given to dissolving the palladium(II) compound in a polyhydric alcohol or sulfoxide, preferably DMSO or glycol, adding the water-soluble phosphine ligand or a solution thereof and adding the resulting catalyst solution to the remaining reactants.

Preference is likewise given to dissolving palladium or a palladium compound in a polyhydric alcohol or sulfoxide, preferably DMSO or glycol, adding the remaining reactants to this solution and subsequently adding the water-soluble phosphine ligand or a solution thereof.

Preference is also given to initially charging the palladium (II) compound, for example in aqueous solution, adding the water-soluble phosphine ligand, if desired as solution, and adding this solution to a mixture of the starting materials, if desired a solvent and the polyhydric alcohol or sulfoxide.

Catalyst systems according to the invention preferably have broad signals of from 36 to 32 ppm and from 8 to 4 ppm in the $^{31}$P-NMR spectrum (with virtual referencing to external 85% phosphoric acid, Bruker DRX 400 spectrometer).

The catalyst systems of the invention display the following reactions: telomerizations, addition of CH-acid compounds onto butadiene, hydrogenations, reactions of nitro compounds, preferably nitroaromatics.

They are therefore used as catalyst in such reactions.

Preference is given to the use as catalyst for carbon-carbon linkage reactions, in particular for the cross-coupling reaction of boronic acids with halogen compounds, preferably aromatic halogen compounds, in particular chloroaromatics.

By way of example, the use of catalyst systems according to the invention for cross-coupling reactions of aromatic boronic acids with haloaromatics is described below.

This reaction comprises reacting a) an aromatic boron compound with b) an aromatic halogen compound or an aromatic perfluoroalkylsulfonate in the presence of c) a base and d) a catalyst system according to the invention.

The catalyst system of the invention is used in the process in an amount of from 0.001 to 10 mol %, preferably from 0.01 to 5 mol %, particularly preferably from 0.05 to 3 mol %, very particularly preferably from 0.05 to 1.5 mol %, based on the aromatic halogen compound or the aromatic perfluoroalkylsulfonate.

Bases which are usually used in the process are alkali metal fluorides, alkali metal and alkaline earth metal hydroxides, alkali metal and alkaline earth metal carbonates, alkali metal hydrogen carbonates, alkali metal and alkaline earth metal acetates, alkali metal and alkaline earth metal alkoxides, and also primary, secondary and tertiary amines.

Particular preference is given to alkali metal fluorides, alkali metal and alkaline earth metal hydroxides, alkali metal and alkaline earth metal carbonates and alkali metal hydrogen carbonates. Very particular preference is given to alkali metal fluorides such as potassium fluoride and cesium fluoride, alkali metal hydroxides such as sodium hydroxide and potassium hydroxide, and also alkali metal carbonates and alkali metal hydrogen carbonates, e.g. lithium carbonate, sodium carbonate and potassium carbonate.

When using solid bases such as $Na_2CO_3$, the polyhydric alcohol or the sulfoxide is preferably used in relatively large amounts or as solvent in order to achieve appropriate suspension of the base and thus a stirrable mixture.

It is naturally also possible to use a plurality of bases.

The base is preferably used in an amount of from 100 to 1000 mol %, particularly preferably from 100 to 500 mol %, very particularly preferably from 100 to 400 mol %, in particular from 100 to 290 mol %, based on the aromatic boron compound.

Preferred starting compounds are, on the one hand, aromatic boron compounds of the formula (XI),

where

Aryl is an aromatic radical and $Q_1$, $Q_2$ are identical or different and are —OH, $C_1$–$C_4$-alkoxy, $C_1$–$C_4$-alkyl, phenyl, which may bear $C_1$–$C_4$-alkyl, C,-$C_4$-alkoxy or halogen substituents, or halogen or $Q_1$ and $Q_2$ together form a $C_1$–$C_4$-alkylenedioxy group or a methylene group which may bear one or two $C_1$–$C_4$-alkyl groups as substituents, or $Q_1$ and $Q_2$ and the boron atom are together part of a boroxane ring of the formula (XI):

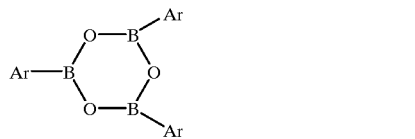

where

Aryl is preferably a phenyl, naphthyl, pyrimidyl, pyridyl, pyrazinyl, pyradiazinyl, 1,3-thiazolyl, 1,3,4-thiadiazolyl or thiophenyl radical, each of which may be unsubstituted or substituted, for example by halogen, cyano, alkyl or alkoxy groups.

Preferably, $Q_1$, $Q_2$ are identical or different and are —OH, $C_1$–$C_4$-alkoxy or halogen or $Q_1$ and $Q_2$ together form a $C_1$–$C_4$-alkylenedioxy group or $Q_1$ and $Q_2$ and the boron atom are together part of a boroxane ring of the formula (XI):

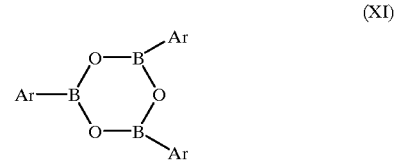

Particularly preferably, Aryl is an unsubstituted or substituted phenyl or naphthyl group.

The aromatic boron compounds used are either known or they can be prepared by methods known per se, as are described, for example, in Houben Weyl, Methoden der Organischen Chemie, Georg Thieme-Verlag, Stuttgart, Volume 13/3a. Thus, for example, boronic acids can be obtained from aromatic alkali metal and magnesium compounds by reaction with trialkoxyboranes and subsequent hydrolysis.

The second class of starting compounds for the process are aromatic compounds of the formula (XII)

where

Aryl is an aromatic radical and

X is Cl, Br, I or a perfluoroalkysulfonate.

X is preferably Cl.

Aryl is preferably an unsubstituted or substituted phenyl, naphthyl, pyridyl, pyrimidyl, pyrazinyl, pyridiazinyl, 1,3-thiazolyl, 1,3,4-thiadiazolyl or thiophenyl radical, where the substituent or substituents is/are, for example, halogen, CN, alkyl, alkoxy or further aryl groups.

The aromatic halogen compounds and perfluoroalkylsulfonates used are either known or can be prepared by known methods, as are described, for example, in Houben Weyl, Methoden der Organischen Chemie, Georg Thieme Verlag, Stuttgart, Volume 5/3 and 5/4. For example, aromatic halides can be obtained by replacing the diazonium group in an appropriate diazonium salt by chlorine, bromine or iodine.

Furthermore, hydroxy-substituted nitrogen heterocycles can be converted into the corresponding halides by means of phosphorus trihalides and phosphorus oxytrihalides.

To carry out the process, the starting materials, the base and the catalyst system of the invention are mixed according to the abovementioned variants and reacted at a temperature of from 0 to 200° C., preferably from 30 to 170° C., particularly preferably from 50 to 150° C., for a period of from 1 to 100 hours, preferably from 5 to 70 hours, particularly preferably from 5 to 50 hours.

The work-up is carried out by known methods with which those skilled in the art are familiar. For example, the product can be separated form the reaction mixture by extraction or precipitation and subsequently be further purified by methods matched to the respective product, for example recrystallization, distillation, sublimation, zone melting, melt crystallization or chromatography.

The compounds prepared in this way are suitable for use as liquid crystal materials or can be used as intermediates for the preparation of further liquid crystal compounds. Furthermore, they are used as precursors for pharmaceuticals, cosmetics, fungicides, herbicides, insecticides, dyes, detergents and polymers, including additives for these.

Various documents have been cited in the present application for example to illustrate the technical field of the invention. All these documents are incorporated by reference into the present application.

The subject matter of the German Patent Applications 195 271 18.1, 195 355 28.8 and 196 200 23.7, whose priority is claimed by the present application, and also the abstract of the present application are hereby expressly incorporated by reference into the present application:

The invention is illustrated by the examples, without being restricted thereby.

EXAMPLES

Example 1

0.388 g of palladium(II) chloride and 0.54 g of sodium acetate are dissolved in 24 ml of DMSO. The mixture is stirred for 30 minutes at room temperature. 14.6 ml of TPPTS/$H_2O$ solution (0.6 mol/l) are subsequently added and the mixture is stirred for another 30 minutes.

Example 2

0.388 g of palladium(II) chloride and 0.54 g of sodium acetate are dissolved in 24 ml of ethylene glycol. The mixture is stirred for another 30 minutes at room temperature. 14.6 ml of TPPTS/$H_2O$ solution (0.6 mol/l) are subsequently added and the mixture is stirred for another 30 minutes.

Example 3

1.069 g of tetrachloropalladic acid (20% by weight of palladium in water) are diluted with 24 ml of water and subsequently admixed with 14.6 ml of a 0.6 molar TPPTS/$H_2O$ solution. The mixture is stirred for another 30 minutes. 50 ml of ethylene glycol are subsequently added.

Immediately after being made up, the solutions display broad signals at from 36 to 32 ppm and from 8 to 4 ppm in the $^{31}$P-NMR spectrum. Referencing was virtual, based on external 85% of phosphoric acid. The spectrometer was a DRX 400 from Bruker.

Use Examples

The mole percentages given for the catalyst solutions refer to the Pd(III) content of the catalyst solution and are based on the halogen compound.

Use Example 1

15 g of 2-chlorobenzonitrile, 14.8 g of p-tolueneboronic acid and 28.9 g of sodium carbonate in 40 ml of glycol and 10 ml of water were heated to 120° C. At 80° C., 0.1 mol % of a catalyst solution prepared as described in Example 1 was added. After the reaction was complete, 50 ml of xylene were added and the organic phase was separated off. Distillation gave 19 g of 2-cyano-4'-methylbiphenyl (b.p. 140° C./mbar).

Comparative Experiment 15 g of 2-chlorobenzonitrile, 14.8 g of p-tolueneboronic acid and 28.9 g of sodium carbonate in 40 ml of glycol and 10 ml of water were heated to 120° C. At 80° C., 0.1 mol % of Pd(O)(TPPTS)$_3$. 9$H_2O$ dissolved in 3 ml of $H_2O$ was added. The reaction mixture was held at 120° C. for 12 hours. After cooling, 50 ml of xylene were added and the organic phase was separated off. Distillation gave 10.5 g of 2-cyano-4'-methylbiphenyl (b.p. 140° C./mbar).

Use Example 2

15 g of 2-chlorobenzonitrile, 14.8 g of p-tolueneboronic acid and 28.9 g of sodium carbonate in 40 ml of glycol and 10 ml of water were heated to 120° C. At 80° C., 0.1 mol % of a catalyst solution prepared as described in Example 2 was added. After the reaction was complete, 50 ml of xylene were added and the organic phase was separated off. Distillation gave 18.5 g of 2-cyano-4'-methylbiphenyl (b.p. 140° C./mbar).

Use Example 3

Preparation of the Catalyst Solution: 0.388 g of palladium (II) chloride and 14.6 ml of TPPTS/$H_2O$ solution (0.6 mol/l) were stirred at room temperature for 60 minutes. This gave a yellow reaction solution of

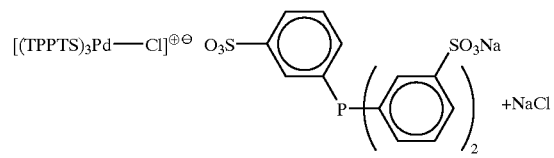

15 g of 2-chlorobenzonitrile, 14.8 g of p-tolueneboronic acid and 28.9 g of sodium carbonate in 40 ml of glycol and 10 ml of water were heated to 120° C. At 80° C., 0.1 mol % of an above-described catalyst solution was added. After the reaction was complete, 50 ml of xylene were added and the organic phase was separated off. Distillation gave 18.7 g of 2-cyano-4'-methylbiphenyl (b.p. 140° C./mbar).

Use Example 4

Preparation of the Catalyst Solution 0.388 g of palladium(II) chloride and 0.33 g of potassium chloride were dissolved in 10 ml of water. 14.6 ml of TPPTS/$H_2O$ solution (0.6 mol/l) were subsequently added.

15 g of 2-chlorobenzonitrile, 14.8 g of p-tolueneboronic acid and 28.9 g of sodium carbonate in 40 ml of glycol and 10 ml of water were heated to 120° C. At 80° C., 0.1 mol % of an above-described catalyst solution was added. After the reaction was complete, 50 ml of xylene were added and the organic phase was separated off. Distillation gave 18.1 g of 2-cyano-4'-methylbiphenyl (b.p. 140° C./mbar).

Use Example 5

15 g of 2-chlorobenzonitrile, 14.8 g of p-tolueneboronic acid and 28.9 g of sodium carbonate in 40 ml of glycol and 10 ml of water were heated to 120° C. At 80° C., 0.1 mol % of a catalyst solution prepared as described in Example 3 was added. After the reaction was complete, 50 ml of xylene were added and the organic phase was separated off. Distillation gave 19 g of 2-cyano-4'-methylbiphenyl (b.p. 140° C./mbar).

Use Example 6

15 g of 2-chlorobenzonitrile, 14.8 g of p-tolueneboronic acid and 12 g of sodium carbonate in 40 ml of glycol and 10 ml of water were heated to 120° C. At 80° C., 0.1 mol % of a catalyst solution prepared as described in Example 1 was added. After the reaction was complete, 50 ml of xylene were added and the organic phase was separated off. Distillation gave 18.5 g of 2-cyano-4'-methylbiphenyl (b.p. 140° C./mbar).

Use Example 7

15 g of 2-chlorobenzonitrile, 14.8 g of p-tolueneboronic acid and 12 g of sodium carbonate in 40 ml of glycol and 10 ml of water were heated to 120° C. At 80° C., 0.1 mol % of a catalyst solution prepared as described in Example 3 was added. After the reaction was complete, 50 ml of xylene were added and the organic phase was separated off. Distillation gave 18.7 g of 2-cyano-4'-methylbiphenyl (b.p. 140° C./mbar).

Use Example 8

15 g of 2-chlorobenzonitrile, 14.8 g of p-tolueneboronic acid and 12 g of sodium carbonate in 40 ml of glycol and 10 ml of water were heated to 120° C. At 80° C., 0.1 mol % of a catalyst solution prepared as described in Example 2 was added. After the reaction was complete, 50 ml of xylene were added and the organic phase was separated off. Distillation gave 18.1 g of 2-cyano-4'-methylbiphenyl (b.p. 140° C./mbar).

Use Example 9

15 g of 2-chlorobenzonitrile, 14.8 g of p-tolueneboronic acid and 28.9 g of sodium carbonate in 50 ml of p-xylene, 40 ml of glycol and 10 ml of water were heated to 120° C. At 80° C., a mixture of 24.7 mg of palladium acetate and 0.55 ml of TPPTS/$H_2O$ solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 18.9 g of 2-cyano-4'-methylbiphenyl.

Use Example 10

15 g of 2-chlorobenzonitrile, 14.8 g of p-tolueneboronic acid and 28.9 g of sodium carbonate in 50 ml of p-xylene, 40 ml of glycerol and 10 ml of water were heated to 120° C. At 80° C., a mixture of 24.7 mg of palladium acetate and 0.55 ml of TPPTS/$H_2O$ solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 18.5 g of 2-cyano-4'-methylbiphenyl.

Use Example 11

15 g of 2-chlorobenzonitrile, 14.8 g of p-tolueneboronic acid and 28.9 g of sodium carbonate in 50 ml of p-xylene, 40 ml of triethylene glycol and 10 ml of water were heated to 120° C. At 80° C., a mixture of 24.7 mg of palladium acetate and 0.55 ml of TPPTS/$H_2O$ solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 17.4 g of 2-cyano-4'-methylbiphenyl.

Use Example 12

15 g of 2-chlorobenzonitrile, 14.8 g of p-tolueneboronic acid and 28.9 g of sodium carbonate in 50 ml of p-xylene, 40 ml of diethylene glycol and 10 ml of water were heated to 120° C. At 80° C., a mixture of 24.7 mg of palladium acetate and 0.55 ml of TPPTS/$H_2O$ solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 18.2 g of 2-cyano-4'-methylbiphenyl.

Use Example 13

15 g of 2-chlorobenzonitrile, 14.8 g of p-tolueneboronic acid and 28.9 g of sodium carbonate in 50 ml of p-xylene, 40 ml of diethanolamine and 10 ml of water were heated to 120° C. At 80° C., a mixture of 24.7 mg of palladium acetate and 0.55 ml of TPPTS/$H_2O$ solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 17.5 g of 2-cyano-4'-methylbiphenyl.

Use Example 14

15 g of 2-chlorobenzonitrile, 14.8 g of p-tolueneboronic acid and 28.9 g of sodium carbonate in 50 ml of p-xylene, 40 ml of triethanolamine and 10 ml of water were heated to 120° C. At 80° C., a mixture of 24.7 mg of palladium acetate and 0.55 ml of TPPTS/$H_2O$ solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 17.8 g of 2-cyano-4'-methylbiphenyl.

Use Example 15

15 g of 2-chlorobenzonitrile, 15.8 g of p-tolueneboronic acid and 15.8 g of potassium fluoride in 50 ml of p-xylene, 40 ml of glycerol and 10 ml of water were heated to 120° C. At 80° C., a mixture of 24.7 mg of palladium acetate and 0.55 ml of TPPTS/$H_2O$ solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 18.2 g of 2-cyano-4'-methylbiphenyl.

Use Example 16

15 g of 2-chlorobenzonitrile, 15.8 g of p-tolueneboronic acid and 15.8 g of potassium fluoride in 50 ml of p-xylene, 40 ml of glycol and 10 ml of water were heated to 120° C. At 80° C., a mixture of 24.7 mg of palladium acetate and 0.55 ml of TPPTS/$H_2O$ solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 18.7 g of 2-cyano-4'-methylbiphenyl.

Use Example 17

15 g of 2-chlorobenzonitrile, 14.8 g of p-tolueneboronic acid and 15.8 g of potassium fluoride in 50 ml of p-xylene, 40 ml of diethylene glycol and 10 ml of water were heated to 120° C. At 80° C., a mixture of 24.7 mg of palladium acetate and 0.55 ml of TPPTS/$H_2O$ solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 17.8 g of 2-cyano-4'-methylbiphenyl.

Use Example 18

15 g of 2-chlorobenzonitrile, 14.8 g of p-tolueneboronic acid and 15.8 g of potassium fluoride in 50 ml of p-xylene, 40 ml of triethylene glycol and 10 ml of water were heated to 120° C. At 80° C., a mixture of 24.7 mg of palladium acetate and 0.55 ml of TPPTS/H$_2$O solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 17.2 g of 2-cyano-4'-methylbiphenyl.

Use Example 19

15 g of 2-chlorobenzonitrile, 14.8 g of p-tolueneboronic acid and 15.8 g of potassium fluoride in 50 ml of p-xylene, 40 ml of diethanolamine and 10 ml of water were heated to 120° C. At 80° C., a mixture of 24.7 mg of palladium acetate and 0.55 ml of TPPTS/H$_2$O solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 16.9 g of 2-cyano-4'-methylbiphenyl.

Use Example 20

15 g of 2-chlorobenzonitrile, 14.8 g of p-tolueneboronic acid and 15.8 g of potassium fluoride in 50 ml of p-xylene, 40 ml of triethanolamine and 10 ml of water were heated to 120° C. At 80° C., a mixture of 24.7 mg of palladium acetate and 0.55 ml of TPPTS/H$_2$O solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 17.2 g of 2-cyano-4'-methylbiphenyl.

Use Example 21

15 g of 2-chlorobenzonitrile, 14.8 g of p-tolueneboronic acid and 28.9 g of sodium carbonate in 50 ml of p-xylene, 40 ml of glycol and 10 ml of water were heated to 120° C. At 80° C., a mixture of 38.66 mg of palladium(II) chloride and 1.1 ml of TPPTS/H$_2$O solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 18.5 g of 2-cyano-4'-methylbiphenyl.

Use Example 22

15 g of 2-chlorobenzonitrile, 14.8 g of p-tolueneboronic acid and 28.9 g of sodium carbonate in 50 ml of p-xylene, 40 ml of glycerol and 10 ml of water were heated to 120° C. At 80° C., a mixture of 38.66 mg of palladium(II) chloride and 1.1 ml of TPPTS/H$_2$O solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 18.2 g of 2-cyano-4'-methylbiphenyl.

Use Example 23

15 g of 2-chlorobenzonitrile, 14.8 g of p-tolueneboronic acid and 28.9 g of sodium carbonate in 50 ml of p-xylene, 40 ml of triethylene glycol and 10 ml of water were heated to 120° C. At 80° C., a mixture of 38.66 g of palladium(II) chloride and 1.1 ml of TPPTS/H$_2$O solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 17.4 g of 2-cyano-4'-methylbiphenyl.

Use Example 24

15 g of 2-chlorobenzonitrile, 14.8 g of p-tolueneboronic acid and 28.9 g of sodium carbonate in 50 ml of p-xylene, 40 ml of diethylene glycol and 10 ml of water were heated to 120° C. At 80° C., a mixture of 38.66 g of palladium(II) chloride and 1.1 ml of TPPTS/H$_2$O solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 17.1 g of 2-cyano-4'-methylbiphenyl.

Use Example 25

15 g of 2-chlorobenzonitrile, 14.8 g of p-tolueneboronic acid and 28.9 g of sodium carbonate in 50 ml of p-xylene, 40 ml of diethanolamine and 10 ml of water were heated to 120° C. At 80° C., a mixture of 38.66 g of palladium(II) chloride and 1.1 ml of TPPTS/H$_2$O solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 17.5 g of 2-cyano-4'-methylbiphenyl.

Use Example 26

15 g of 2-chlorobenzonitrile, 14.8 g of p-tolueneboronic acid and 28.9 g of sodium carbonate in 50 ml of p-xylene, 40 ml of triethanolamine and 10 ml of water were heated to 120° C. At 80° C., a mixture of 38.66 g of palladium(II) chloride and 1.1 ml of TPPTS/H$_2$O solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 17.8 g of 2-cyano-4'-methylbiphenyl.

Use Example 27

15 g of 2-chlorobenzonitrile, 14.8 g of p-tolueneboronic acid and 15.8 g of potassium fluoride in 50 ml of p-xylene, 40 ml of glycerol and 10 ml of water were heated to 120° C. At 80° C., a mixture of 38.66 mg of palladium(II) chloride and 1.1 ml of TPPTS/H$_2$O solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 18.9 g of 2-cyano-4'-methylbiphenyl.

Use Example 28

15 g of 2-chlorobenzonitrile, 14.8 g of p-tolueneboronic acid and 15.8 g of potassium fluoride in 50 ml of p-xylene, 40 ml of glycol and 10 ml of water were heated to 120° C. At 80° C., a mixture of 38.66 mg of palladium(II) chloride and 1.1 ml of TPPTS/$H_2O$ solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 18.8 g of 2-cyano-4'-methylbiphenyl.

Use Example 29

15 g of 2-chlorobenzonitrile, 14.8 g of p-tolueneboronic acid and 15.8 g of potassium fluoride in 50 ml of p-xylene, 40 ml of diethylene glycol and 10 ml of water were heated to 120° C. At 80° C., a mixture of 38.66 mg of palladium(II) chloride and 1.1 ml of TPPTS/$H_2O$ solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 18.0 g of 2-cyano-4'-methylbiphenyl.

Use Example 30

15 g of 2-chlorobenzonitrile, 14.8 g of p-tolueneboronic acid and 15.8 g of potassium fluoride in 50 ml of p-xylene, 40 ml of triethylene glycol and 10 ml of water were heated to 120° C. At 80° C., a mixture of 38.66 mg of palladium(II) chloride and 1.1 ml of TPPTS/$H_2O$ solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 16.9 g of 2-cyano-4'-methylbiphenyl.

Use Example 31

15 g of 2-chlorobenzonitrile, 14.8 g of p-tolueneboronic acid and 15.8 g of potassium fluoride in 50 ml of p-xylene, 40 ml of diethanolamine and 10 ml of water were heated to 120° C. At 80° C., a mixture of 38.66 mg of palladium(II) chloride and 1.1 ml of TPPTS/$H_2O$ solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 17.1 g of 2-cyano-4'-methylbiphenyl.

Use Example 32

15 g of 2-chlorobenzonitrile, 14.8 g of p-tolueneboronic acid and 15.8 g of potassium fluoride in 50 ml of p-xylene, 40 ml of triethanolamine and 10 ml of water were heated to 120° C. At 80° C., a mixture of 38.66 mg of palladium(II) chloride and 1.1 ml of TPPTS/$H_2O$ solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 18.0 g of 2-cyano-4'-methylbiphenyl.

Use Example 33

15 g of 2-chlorobenzonitrile, 14.8 g of p-tolueneboronic acid and 28.9 g of sodium carbonate in 50 ml of p-xylene, 40 ml of glycol and 10 ml of water were heated to 120° C. At 80° C., 19.3 mg of palladium chloride, 17.9 mg of sodium acetate and 0.55 ml of TPPTS/$H_2O$ solution (0.6 molar) in 2.5 ml of DMSO were added. After the reaction was complete, the phases were separated. The aqueous phase was washed with 50 ml of toluene. The combined organic phases were washed with 20 ml of water and subsequently dried over sodium sulfate. Crystallization from n-heptane gave 18.7 g of 2-cyano-4'-methylbiphenyl.

Use Example 34

15 g of 2-chlorobenzonitrile, 14.8 g of p-tolueneboronic acid and 28.9 g of sodium carbonate in 50 ml of p-xylene, 40 ml of glycerol and 10 ml of water were heated to 120° C. At 80° C., a mixture of 19.3 mg of palladium chloride, 17.9 mg of sodium acetate and 0.55 ml of TPPTS/$H_2O$ solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 18.3 g of 2-cyano-4'-methylbiphenyl.

Use Example 35

15 g of 2-chlorobenzonitrile, 14.8 g of p-tolueneboronic acid and 28.9 g of sodium carbonate in 50 ml of p-xylene, 40 ml of triethylene glycol and 10 ml of water were heated to 120° C. At 80° C., a mixture of 19.3 mg of palladium chloride, 17.9 mg of sodium acetate and 0.55 ml of TPPTS/$H_2O$ solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 17.4 g of 2-cyano-4'-methylbiphenyl.

Use Example 36

15 g of 2-chlorobenzonitrile, 14.8 g of p-tolueneboronic acid and 28.9 g of sodium carbonate in 50 ml of p-xylene, 40 ml of diethylene glycol and 10 ml of water were heated to 120° C. At 80° C., a mixture of 19.3 mg of palladium chloride, 17.9 mg of sodium acetate and 0.55 ml of TPPTS/$H_2O$ solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 18.3 g of 2-cyano-4'-methylbiphenyl.

Use Example 37

15 g of 2-chlorobenzonitrile, 14.8 g of p-tolueneboronic acid and 28.9 g of sodium carbonate in 50 ml of p-xylene, 40 ml of diethanolamine and 10 ml of water were heated to 120° C. At 80° C., a mixture of 19.3 mg of palladium chloride, 17.9 mg of sodium acetate and 0.55 ml of TPPTS/$H_2O$ solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 17.5 g of 2-cyano-4'-methylbiphenyl.

Use Example 38

15 g of 2-chlorobenzonitrile, 14.8 g of p-tolueneboronic acid and 28.9 g of sodium carbonate in 50 ml of p-xylene, 40 ml of triethanolamine and 10 ml of water were heated to 120° C. At 80° C., 19.3 mg of palladium chloride, 17.9 mg of sodium acetate and 0.55 ml of TPPTS/$H_2O$ solution (0.6 molar) in 2.5 ml of DMSO were added. After the reaction was complete, the phases were separated. The aqueous phase was washed with 50 ml of toluene. The combined organic phases were washed with 20 ml of water and subsequently dried over sodium sulfate. Crystallization from n-heptane gave 17.8 g of 2-cyano-4'-methylbiphenyl.

Use Example 39

15 g of 2-chlorobenzonitrile, 14,8 g of p-tolueneboronic acid and 28.9 g of sodium carbonate in 50 ml of p-xylene, 40 ml of DMSO and 10 ml of water were heated to 120° C. At 80° C., a mixture of 24.7 mg of palladium(II) acetate and 0.55 ml of TPPTS/$H_2O$ (0.6 molar) in 2.5 ml of DMSO was added.

After the reaction was complete, the phases were separated. The aqueous phase was washed with 50 ml of xylene. The combined organic phases were washed with 20 ml of water and subsequently dried over sodium sulfate. The solvent was evaporated and the residue was crystallized form n-heptane. Yield: 18.6 g (88% of theory) of 2-cyano-4'-methylbiphenyl.

Use Example 40

15 g of 2-chlorobenzonitrile, 14,8 g of p-tolueneboronic acid and 28.9 g of sodium carbonate in 50 ml of p-xylene, 40 ml of DMSO and 10 ml of water were heated to 120° C. At 80° C., a mixture of 38.66 mg of palladium(II) chloride and 1.1 ml of TPPTS/$H_2O$ solution (0.6 molar) in 2.5 ml of DMSO was added. After the reaction was complete, the phases were separated. The aqueous phase was washed with 50 ml of xylene. The combined organic phases were washed with 20 ml of water and subsequently dried over sodium sulfate. The solvent was evaporated and the residue was crystallized from n-heptane. Yield: 18.2 g (86% of theory) of 2-cyano-4'-methylbiphenyl.

Use Example 41

15 g of 2-chlorobenzonitrile, 14.8 g of p-tolueneboronic acid and 28.9 g of sodium carbonate in 50 ml of p-xylene, 40 ml of DMSO and 10 ml of water were heated to 120° C. At 80° C., a mixture of 19.3 mg of palladium(II) chloride, 17.9 mg of sodium acetate and 0.55 ml of TPPTS/$H_2O$ solution (0.6 molar) in 2.5 ml of DMSO was added. After the reaction was complete, the phases were separated. The aqueous phase was washed with 50 ml of xylene. The combined organic phases were washed with 20 ml of water and subsequently dried over sodium sulfate. The solvent was evaporated and the residue was crystallized from n-heptane. Yield: 18.8 g (89% of theory) of 2-cyano-4'-methylbiphenyl.

Use Example 42

15 g of 2-chlorobenzonitrile, 14.8 g of p-tolueneboronic acid and 28.9 g of sodium carbonate in 50 ml of p-xylene and 40 ml of DMSO were heated to 120° C. At 80° C., a mixture of 24.7 mg of palladium(II) acetate and 0.55 ml of TPPTS/$H_2O$ solution (0.6 molar) in 2.5 ml of DMSO was added. After the reaction was complete, the phases were separated. The aqueous phase was washed with 50 ml of xylene. The combined organic phases were washed with 20 ml of water and subsequently dried over sodium sulfate. The solvent was evaporated and the residue was crystallized from n-heptane. Yield: 18.0 g (85% of theory) of 2-cyano-4'-methylbiphenyl.

Use Example 43

Cross-coupling of 2-chlorobenzonitrile with 4-tolueneboronic acid.

To prepare the catalyst, 38.8 mg (0.219 mmol) of palladium(II) chloride and 54.0 mg (0.657 mmol) of sodium acetate in 2.4 ml of DMSO are stirred for 30 minutes at 23° C. in an argon atmosphere. Subsequently, 1.99 ml (0.875 mmol) of a 0.44 molar aqueous solution of sodium 4-diphenylphosphinophenylphosphinate, prepared as described below, are added and the suspension is stirred at 23° C. for another 30 minutes. Under an argon atmosphere, 30.0 g (0.2181 mol) of 2-chlorobenzonitrile, 32.6 g (0.240 mol) of 4-tolueneboronic acid and 16.2 g (70 mol %) of sodium carbonate are stirred in 120 ml of ethylene glycol. 20 ml of water are added and the mixture is heated to 80° C. The above-described catalyst suspension is then added and the mixture is heated under reflux for 5 hours. At 23° C., the mixture is admixed with 100 ml of ethyl acetate. The organic phase is separated off evaporated on a rotary evaporator and fractionally distilled under reduced pressure. This gives 31.6 g (75% of theory) of 2-cyano-4'-methlbiphenyl (b.p. 140° C./1.0 mbar; m.p. 50° C.).

What is claimed is:
1. A catalyst system obtained by reacting:
a) a palladium(II) compound with;
b) a water-soluble phosphine ligand; and
c) a sulfoxide or polyhydric alcohol.
2. A catalyst system as claimed in claim 1, wherein the polyhydric alcohol is water-soluble and is selected from the group consisting of glycols, glycerol, oligoglycerides, which may also be partially esterified, diethylene, triethylene and tetraethylene glycols or polyethylene glycols of the formula (VIII),

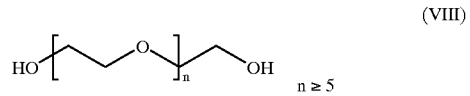

(VIII)

polyhydric alkanols or alkenols, polyhydric cycloalkanols, polyhydric alkanols containing aryl groups, polyhydric aminoalcohols, polyhydric iminoalcohols or 1,1',1"-nitrilotri-2-propanol, 1,3,5-tri(2-hydroxyethyl)isocyanuric acid and dihydroxyacetone.
3. A catalyst system as claimed in claim 1, wherein the sulfoxide used has the formula (IX)

(IX)

where $R^1$, $R^2$ are aliphatic or aromatic hydrocabons which may be substituted or linked to one another.
4. A catalyst system as claimed in claim 1, wherein the water-soluble phosphine ligand is selected from the group consisting of tri-n-alkylphosphines, triarylphosphines, dialkylarylphosphines, alkyldiarylphosphines and heteroarylphosphines provided with carboxylate or carboxylic acid, ammonium, phosphonium, sulfonate or sulfonic acid, phosphonate or phosphonic acid groups or with polyalcohols having a suitable number of hydroxy functions or polyalkylene glycols having a suitable chain length, where the three substituents on the phosphorus can be identical or different and chiral or achiral and one or more of the substituents can link the phosphorus groups of a plurality of phosphines and part of this linkage can also be one or more metal atoms.

5. A catalyst system as claimed in claim 1, wherein the palladium(II) compound used is selected from the group consisting of palladium(II) salts, tetrachloropalladic acid or salts thereof.

6. A process for preparing a catalyst system which comprises reacting:
   a) a palladium(II) compound with;
   b) a water-soluble phosphine ligand; and
   c) a sulfoxide or polyhydric alcohol.

7. The process as claimed in claim 6, wherein water is added to the reaction.

8. The process as claimed in claim 6, wherein a solubilizer for the palladium compound is added.

9. The process as claimed in claim 8, wherein the solubilizer is sodium acetate.

10. A method for carrying out C—C linkage reactions using a catalyst system, said catalyst system is obtained by:
   reacting a palladium(II) compound with a water-soluble phosphine ligand and a sulfoxide or polyhydric alcohol, said method comprising cross-coupling an aromatic boron compound with an aromatic halogen compound or perfluoroalkylsulfonate in the presence of a base and said catalyst system.

* * * * *